United States Patent [19]
Loree, II et al.

[11] Patent Number: 5,887,985
[45] Date of Patent: Mar. 30, 1999

[54] WEAR-RESISTANT BEARINGS

[75] Inventors: Howard M. Loree, II, Cambridge; David B. Gernes, Watertown; Anthony J. Armini, Manchester; Dennis A. Gadarowski, Billerica, all of Mass.

[73] Assignee: Thermo Cardiosystems Inc., Woburn, Mass.

[21] Appl. No.: 899,689

[22] Filed: Jul. 24, 1997

[51] Int. Cl.$^6$ .................................................. F16C 33/62
[52] U.S. Cl. .................................... 384/492; 384/625
[58] Field of Search .......................... 384/42, 276, 297, 384/492, 569, 625, 907, 907.1, 912, 913

[56] References Cited

U.S. PATENT DOCUMENTS

| | | | |
|---|---|---|---|
| 3,640,689 | 2/1972 | Glaski et al. | 29/195 |
| 3,988,955 | 11/1976 | Engel et al. | 83/661 |
| 4,433,005 | 2/1984 | Manty et al. | 427/38 |
| 4,540,636 | 9/1985 | MacIver et al. | 428/610 |
| 4,554,208 | 11/1985 | MacIver et al. | 428/332 |
| 4,565,710 | 1/1986 | Singer et al. | 427/35 |
| 4,568,396 | 2/1986 | Vardiman | 148/133 |
| 4,618,505 | 10/1986 | MacIver et al. | 427/38 |
| 4,629,631 | 12/1986 | Dearnaley | 427/38 |
| 4,707,238 | 11/1987 | Okubo | 204/192.31 |
| 4,754,494 | 6/1988 | Kumar | 384/297 X |
| 4,824,262 | 4/1989 | Kamigaito et al. | 384/276 X |
| 4,828,728 | 5/1989 | Dimigen et al. | 252/12 |
| 4,838,710 | 6/1989 | Ohta et al. | 384/100 |
| 4,848,934 | 7/1989 | Blakely et al. | 384/206 |
| 4,858,294 | 8/1989 | Hollox | 29/149.5 R |
| 4,859,493 | 8/1989 | Lemelson | 427/45.1 |
| 4,872,922 | 10/1989 | Bunker et al. | 148/4 |
| 4,902,652 | 2/1990 | Kume et al. | 501/90 |
| 4,956,858 | 9/1990 | Upadhya | 378/133 |
| 4,960,643 | 10/1990 | Lemelson | 428/408 |
| 5,059,038 | 10/1991 | Domes | 384/104 |
| 5,079,032 | 1/1992 | Oliver | 427/38 |
| 5,133,757 | 7/1992 | Sioshansi et al. | 623/18 |
| 5,165,804 | 11/1992 | Fisher et al. | 384/492 |
| 5,208,079 | 5/1993 | Fukushima et al. | 427/527 |
| 5,284,394 | 2/1994 | Lemelson | 384/463 |
| 5,290,070 | 3/1994 | Deits et al. | 384/625 |
| 5,322,735 | 6/1994 | Fridez et al. | 428/357 |
| 5,443,663 | 8/1995 | Meletis | 148/222 |
| 5,447,291 | 9/1995 | Sandhage | 264/60 |
| 5,455,081 | 10/1995 | Okada et al. | 427/528 |
| 5,466,305 | 11/1995 | Sato et al. | 148/222 |
| 5,549,764 | 8/1996 | Biltgen et al. | 148/222 |
| 5,554,415 | 9/1996 | Turchan et al. | 427/248.1 |
| 5,562,730 | 10/1996 | Davidson | 623/3 |

OTHER PUBLICATIONS

Alonso et al., "Changes in Tribulogical Properties of an AISI 440C Martensitic Stainless Steel After Ion Implantation of Carbon at Very High Doses," *Surface and Coatings Technology*, 83 (1996) 263–268.

Dearnaley, "Practical Applications of Ion Implantation," *Journal of Metals*, Sep. 1982, pp. 18–28.

Kobs et al., "Strong Wear Reduction of High–Dose Carbon–Implanted AISI 52100 Steel," *Nuclear Instruments and Methods in Physics Research*, B59/60 (1991) 746–750.

Kustas et al., "Effects of Ion Implantation of the Rolling Contact Fatigue of 440C Stainless Steel," *Mat. Res. Soc. Symp. Proc.*, vol. 27 (1984), pp. 685–690.

Pope et al., "Effects of Ion Implantation on Friction and Wear of Stainless Steels," *ASME: International Conference on Wear of Materials*, 1983, pp. 280–287.

(List continued on next page.)

*Primary Examiner*—Thomas R. Hannon
*Attorney, Agent, or Firm*—Fish & Richardson P.C.

[57] ABSTRACT

A bearing includes a first component having a surface and a second component having a surface moveable relative to the surface of the first component and contacting that surface when the components are at rest relative to each other. The surface of the second component is coated with a ceramic material and the surface of the second component is implanted with ions. The bearing can be used in an implantable heart pump.

24 Claims, 4 Drawing Sheets

OTHER PUBLICATIONS

Pope et al., "Friction and Wear Reductin of 440C Stainless Steel by Ion Implantation," *Mat. Res. Soc. Symp. Proc.,* vol. 27 (1984), pp. 661–666.

"Standard Test Method for Wear Testing With a Pin-on-Disk Apparatus," *ASTM: Designation: G99–95,* (Apr. 1995), pp. 386–390.

"Data Sheet Collection on Vilab Coated TIVIC and TiC Balls," *Vilab Ltd.,* 1994.

"Design News," *A Cahners Publication,* Feb. 10, 1992.

WEAR-RESISTANT BEARINGS

BACKGROUND OF THE INVENTION

This invention relates to a novel combination of materials for use as wear-resistant bearings, in particular, wear-resistant bearings used in artificial heart pumps.

Bearings comprise two contacting surfaces, which support varying loads while allowing relative motion between the contacting surfaces. Typical bearings include ball and other rolling-element bearings as well as journal-type bearings. Many bearings utilize lubricants, which cushion one surface from another when there is relative motion between the two surfaces. In particular, if two surfaces move relative to one another and fluid is introduced between them, a pressure gradient forms between the two surfaces preventing surface to surface contact and significantly reducing friction. For example, in a ball bearing, the ball typically rolls on a cushion of lubricant.

Reducing friction in lubricated bearings requires the following conditions. First, the relative velocity between the two surfaces must exceed a threshold velocity. Second, a sufficient volume of lubricant must be present. Third, surfaces must be smooth enough so that any surface roughness or asperities have heights that are less than the thickness of the lubricant. Even under these conditions, surfaces still come into contact from time to time and friction is increased. This can especially occur during heavy loading or irregular velocity.

When the two surfaces that move relative to one another come into contact, a phenomenon known as cold welding can occur. In cold welding, surface asperities from one surface weld to the other surface, and as the surfaces move, the welded asperities are pulled from their original surface forming pits in the base metal of that surface. Most of the welding asperities will separate from both surfaces becoming wear particles, which contaminate the lubricant. As the lubricant breaks down due to contamination, friction between the surfaces increases, thereby accelerating the production of wear particles and further breakdown.

It is often desirable to reduce wear in bearings and consequently increase the longevity of the bearings. One approach to reducing wear is the use of dissimilar materials for different surfaces of the bearing, reducing wear associated with cold welding. Another approach to reducing wear is the ion-implantation of one or both of the bearing surfaces. This approach is not completely understood, but it reduces friction between bearing surfaces in some cases. Nonetheless, even with these approaches, the wear properties of bearings vary widely depending on the particular surface materials and treatments.

SUMMARY OF THE INVENTION

The invention features a novel combination of materials for the contacting surfaces of a bearing, providing improved wear-resistance and reduced friction. A first surface of the bearing has a ceramic coating, such as titanium carbide. A second surface of the bearing that contacts the first surface is heavily implanted with ions. Wear-resistant bearings having these features can be used in any application where long life is important, for example, they can be used advantageously in an artificial heart pump.

In general, in one aspect, the invention features a bearing that includes a first component having a surface and a second component having a surface moveable relative to the surface of said first component and contacting the surface of said first component when the components are at rest relative to each other. The surface of the first component is coated with a ceramic material and the surface of the second component is implanted with ions.

The bearing can have any of the following features. The ceramic material coated on the surface of the first component can be one of titanium carbide, titanium nitride or silicon nitride, in particular, it can be titanium carbide. The surface of the second component can be implanted with carbon ions. The surface density of the implanted carbon ions can be greater than about $1\times10^{18}$ ion/cm$^2$, or about $3\times10^{18}$ ion/cm$^2$, and the penetration of the carbon ions into the surface of the second component corresponds to carbon ion implantation at a beam energy of greater than about 50 keV. The first component of the bearing can be a rolling element, such as a ball, and the rolling element can be metal, in particular, it can be a 440C stainless steel ball. The second component of the bearing can be a raceway, in particular, it can be a BG-42 stainless steel raceway.

In another aspect, the invention features a bearing for use in an implantable heart pump, that includes a first component having a surface and a second component having a surface moveable relative to the surface of said first component and contacting the surface of said first component when the components are at rest relative to each other. The surface of the first component is coated with a ceramic material and the surface of the second component is implanted with ions. The bearing for use in the implantable heart pump can have any of the features described in the previous paragraph.

In another aspect, the invention features a bearing having a titanium-carbide coated 440C stainless steel ball contacting, when at rest, a BG-42 stainless steel raceway implanted with carbon ions to a density greater than about $1\times10^{18}$ ions/cm$^2$ at a beam energy of greater than about 50 kev.

In another aspect, the invention features a method of making a bearing using the following steps: 1) providing a first component having a ceramic surface; 2) implanting ions into a surface of a second component; and 3) forming a bearing from the first and second components, in which the surfaces contact each other, when at rest. During the implanting step, the carbon ions can be implanted to a density greater than about $1\times10^{18}$ ions/cm$^2$ and at a beam energy greater than about 50 kev. Also, the ceramic surface can include titanium carbide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. The disclosure of all publications, patent applications, patents, and other references mentioned herein are incorporated by reference in their entirety. In case of conflict, the present specification, including definitions, will control. In addition, the materials, methods, and examples are illustrative only and not intended to be limiting.

Bearings constructed according to the invention are particularly suited for use in heart pumps, e.g., implantable ventricular-assist devices where longevity and variable cyclical loading place extraordinary demands on bearing surfaces.

Other features and advantages of the invention will be apparent from the following detailed description and from the claims.

DESCRIPTION OF THE PREFERRED EMBODIMENTS

The invention features a bearing having the combination of a first surface with a ceramic coating and a second surface heavily implanted with ions in movable contact with the first surface. In the following description, we will first describe the mechanical design of the bearing. Second, we will describe the ceramic coating and the ion implantation of the bearing. Third, we will show experimental results demonstrating profound reductions in friction and wear for the bearing. Finally, we will describe using the wear-resistant bearings in implantable heart pumps.

Bearings Types and Materials

Any of the following bearing types and materials can be used in the invention.

Figure 1:
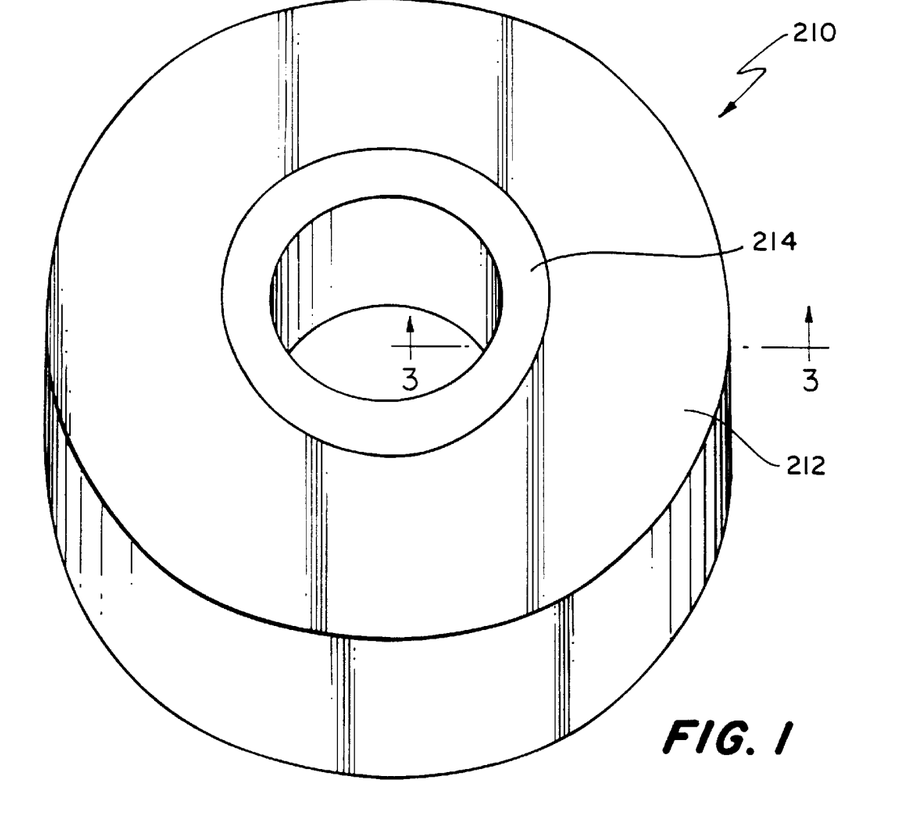
FIG. 1 is a perspective view of a typical ball bearing.
Figure 2:
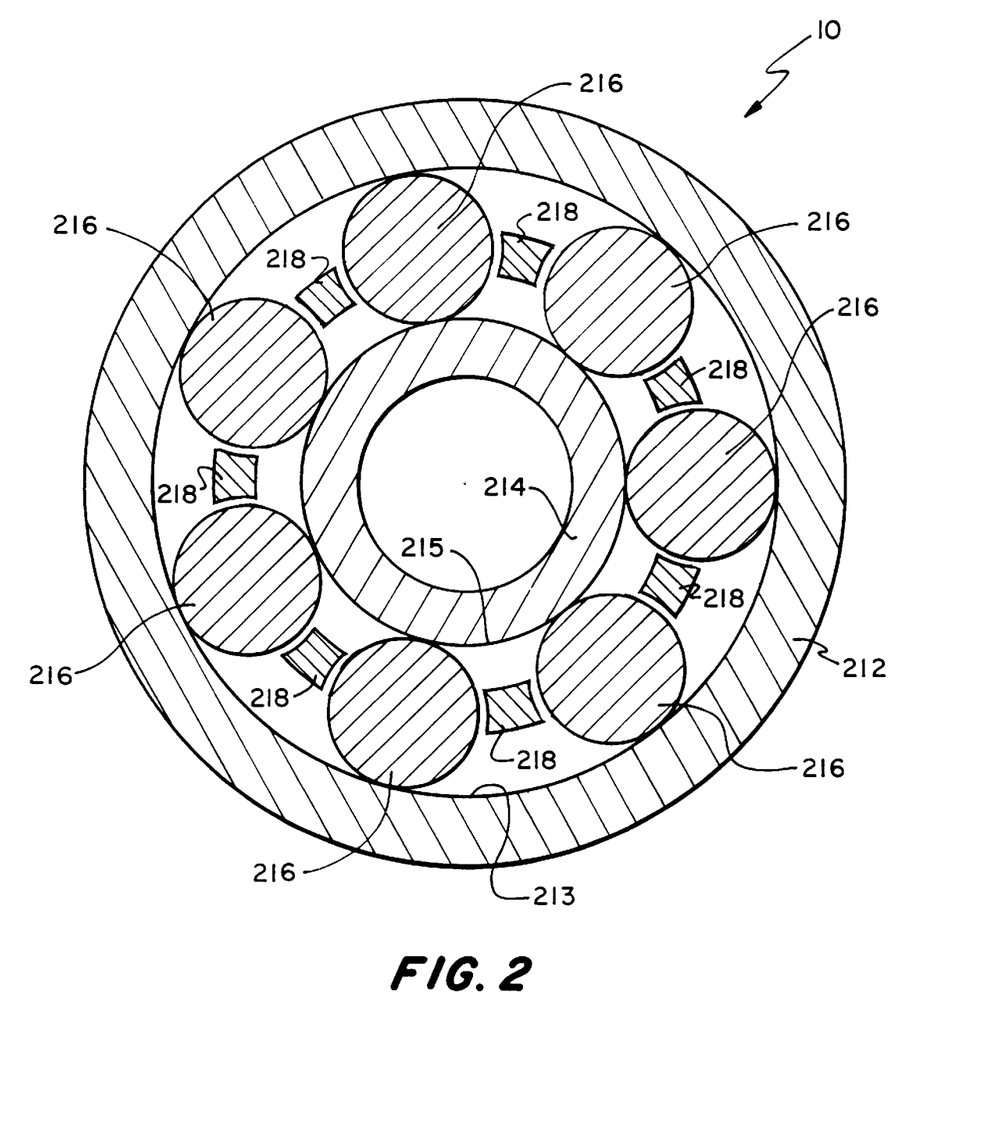
FIG. 2 is a cross-sectional view of the bearing in FIG. 1.

An example of a ball bearing 210 is shown in FIG. 1. The bearing includes an outer ring-shaped component 212 and a concentric inner ring-shaped component 214. Components 212 and 214 can rotate relative to one another about their common axis, even when the components carry a load. Sandwiched between components 212 and 214 are a plurality of balls 216, as shown in FIG. 2, which is a cross-sectional view of bearing 210 within the plane of the ring shaped components. Balls 216 roll along both of the inner surfaces 213 and 215 of components 212 and 214, respectively. The rolling balls allow components 212 and 214 to rotate relative to one another with reduced friction and support the components when loads on the bearing press them together. The balls are held within a cage 218, which keep the balls spaced from one another. Typically, the bearing will also include lubricant to further decrease the friction between balls 216 and the surfaces of components 212 and 214 on which the balls roll.

Figure 3:
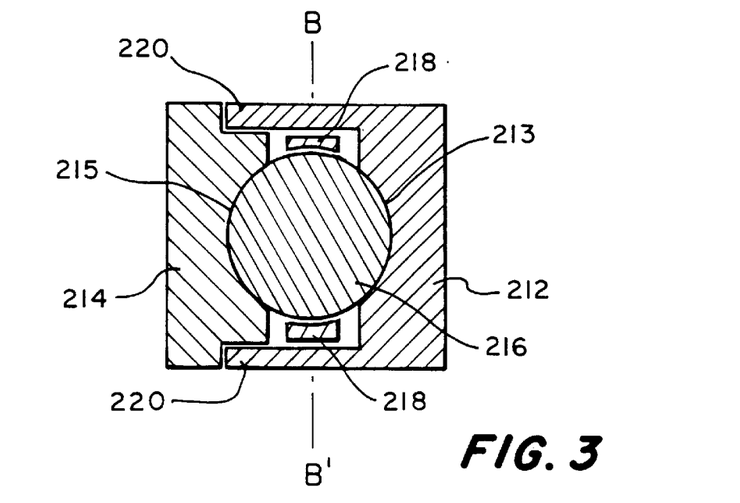
FIG. 3 is a cross-sectional view of the bearing in FIG. 1 along the plane 3—3.

The contacting surfaces of bearing 210 are also shown in FIG. 3, which is a cross-sectional view along the line 3—3 in FIG. 1. Cage 218 maintains ball 216 along the axis B–B', about which ball 216 rolls. The rolling surfaces of ball 216 contacts surfaces 213 and 215, however the geometry of the rolling ball minimize the friction associated with that contact. Components 212 and 214 are not in direct contact with one another, but component 212 can include outer lips 220 which prevent contaminants from reaching the contacting surfaces and degrading the lubricant therebetween.

Bearing 210 is an example of a rolling element bearing. In other types of rolling element bearings, the rolling elements (i.e., the balls) can be replaced with, for example, cylinders, tapered cylinders, double-row cylinders, barrels, or needles. The surfaces on which the rolling elements roll are shaped to match the rolling element. Ball bearings are typically used for relatively low loads, whereas straight or tapered rollers are typically used for heavier loads.

Another type of bearing is a journal bearing, in which an inner cylinder, along with lubricant, lies along the inner surface of a hollow outer cylinder. As the inner cylinder turns relative to the outer cylinder, a pressure gradient is formed across the lubricant, and the lubricant lifts the inner cylinder from the inner surface of the outer cylinder.

In general, the surface on which the balls or rollers roll in a bearing is referred to as the raceway. For a general reference on bearings, see: Harris, T. A., *Rolling Bearing Analysis*, 3rd Ed. (John Wiley and Sons, Inc., New York, 1991).

Optimum bearing materials combine high hardness and high wear-resistance. Some common materials are 52100 bearing steel, which is a high carbon steel alloy, and stainless steel, which includes chromium to prevent corrosion and can be tempered to a high hardness. For bio-medical application 440C stainless steel (a particular alloy of stainless steel) is desirable even though it is typically more expensive than 52100 bearing steel. Most preferably, BG-42 stainless steel, a variant of 440C stainless steel, is used. BG-42 stainless steel is a vacuum remelted alloy having very few voids and a very uniform surface profile. For a specification on BG-42, see: Society for Aerospace Engineering (SAE) *Aerospace Material Specification* #AMS 5749C (1992). Other metal alloys which can be used for bearings include alloys formed by compressed powdered metallurgy (CPM), such as CPM440V and CPM10V. In CPM, the alloys are formed by compression rather than melting. In some cases, bearing materials could also include alloys such as bronze and brass.

For high speed and low-weight applications, bearing rolling elements are also made out of ceramic materials such as silicon nitride ($Si_3N_4$).

Treatment of the Bearing Surfaces

One of the contacting surfaces of the bearing, i.e., either the rolling element or the raceway, is coated with a ceramic material. Suitable ceramic materials can include, for example, titanium carbide (TiC), titanium nitride (TiN), and silicon nitride ($Si_3N_4$);

Vilab Ltd. (Berne, Switzerland) has optimized a technique for coating 440C stainless steel balls with titanium carbide (TiC) and makes TiC-coated stainless steel balls which are commercially available. More information regarding the TiC-coated balls can be found in *Data sheet collection on Vilab coated and TIVIC and TiC Balls* (Vilab Ltd., January 1994).

The other contacting surface of the bearing, i.e., the rolling element or raceway that is not coated with a ceramic material, is treated by ion-implantation. Ion implantation is a technique for changing the surface properties of metals or plastics. In ion implantation, a target piece (e.g., the contacting bearing surface not coated with a ceramic material) is placed in a high vacuum chamber and exposed to a beam of ions. The ions are generated by exposing a gas to a high-voltage source. Then, the ions are manipulated and accelerated, using magnets and scanning coils, into an ion beam containing selected ion species having a selected range of kinetic energies. The techniques is "line of sight" by nature (i.e. only those regions of the surface exposed to the ion beam will be implanted). For implantation of components having complicated surfaces, careful rotation and translation of the component are required to implant the surface completely and uniformly.

The properties of the implanted surface depend on the following parameters: 1) the ion species being implanted and the nature of the target material; 2) the kinetic energy of the ions, which determines how deeply the ion can penetrate the surface to be implanted; and 3) the ion beam current (i.e., then number of ions per unit time per unit area), which determines how quickly ions implant and the density of implanted ions over a period of time (i.e. number of implanted ions per unit area of surface). Typically, the energy of the ion beam is stated as a potential, e.g. 90 kilo electron volts (kev), which indicates the potential used to accelerate the ion. For the same potential, the kinetic energy of a given ion is proportional to its charge. An additional concern is thermal excitation of the target sample. During implantation, the impinging ions will heat up the target sample. One must be careful that this increase in temperature does not approach a temperature at which the surface structure undergoes thermally-assisted rearrangement. Ion implantation is described in greater detail in G. Dearnaley (*Journal of Metals*, September 1982, pages 18–28).

Ion implants for the contacting surface of the bearing not coated with a ceramic material can include, for example, carbon (C), titanium (Ti), chromium (Cr), nitrogen (N), and combinations thereof. The ion beam energies can be between about 50 to 200 kev and ion surface densities can be between about $1 \times 10^{16}$ to $1 \times 10^{19}$ ions/cm$^2$. The depth of ion implantation is typically about 200 to 300 nm. For more information on ion implantation see: K. Kobs et al. (*Nuclear Instruments and Methods in Physics Research*, B59/60:746–750, 1991) and Zaretsky, E.V., *STLE Life Factors for Rolling Bearings* pp. 116–117 (STLE, Park Ridge, Ill., 1992). There are also many companies that specialize in ion implantation, for example Implant Sciences, Corp. (Wakefield, Mass.).

Bearing Properties

Wear and friction experiments were performed on a variety of combinations of treated and untreated materials used for the contacting surfaces of a bearing. Most preferable results, reflecting significantly reduced wear and friction, were achieved by a bearing having a TiC-coated 440C stainless steel ball rolling on a ion-implanted BG-42 stainless steel raceway. The BG-42 disk raceway was implanted with a beam of carbon ions to a density of greater than $1 \times 10^{18}$ ions/cm$^2$, e.g., a density of about $3 \times 10^{18}$ ions/cm$^2$, at a beam energy of between 70 and 160 kev -e.g., about 90 kev.

Figure 4:
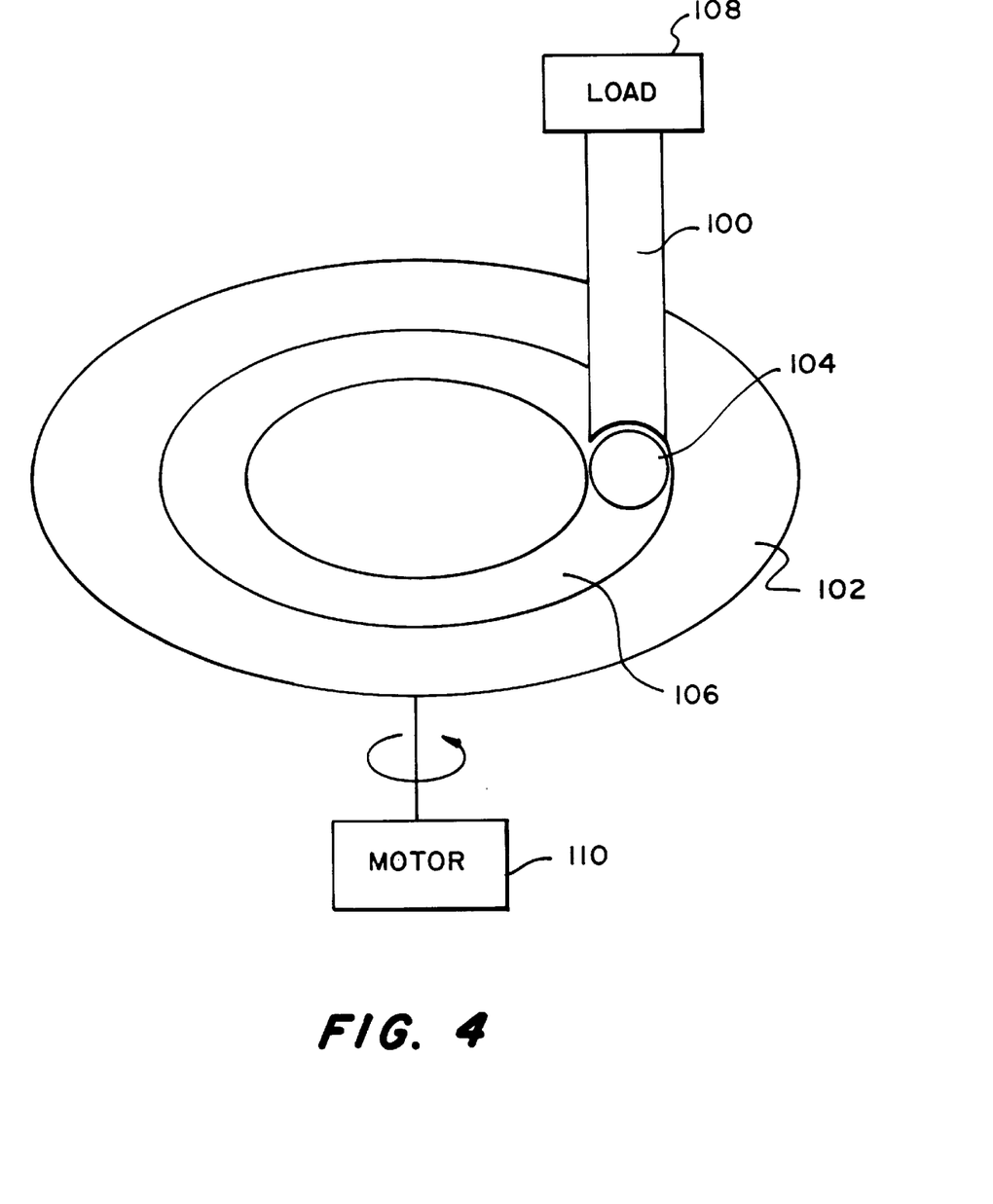
FIG. 4 is a schematic of an apparatus used in a pin on disk test.

Wear and friction measurements were performed using a "pin-on-disk" test using an apparatus shown schematically in FIG. 4. Pin-on-disk tests are the American Society for Testing and Measurement (ASTM) standard for measuring wear and friction, see: ASTM G99–95, *Standard test method for wear testing with a pin-on-disk test* (ASTM, Philadelphia, Pa. 1995). In a pin-on-disk test, a stationary pin 100 having an applied load 108 is placed on a moving disk 102 rotating at a constant speed, much like a stylus on record in a record player. The pin 100 represents the stationary element of a bearing couple and the disk 102 represents the moving element of a bearing couple. The test is used to measure three things: the friction coefficient during the test; the volume of material removed from the pin 100 by the end of the test; and the volume of material removed from the wear track 106 in the disk 102 by the end of the test. To determine the friction coefficient, the current demands of a motor 110 used to rotate the disk 102 are measured as a function of the applied load 108. Pin-on-disk tests are performed without lubrication and so they are good model for the worse case scenario of complete breakdown of a lubricated bearing. For ball bearings, the pin 100 has the ball 104 to be studied attached to its end, so that the ball 104 contacts the disk 102.

Pin-on-disk test were conducted for each of the combinations listed below in Table 1.

TABLE 1

Wear Data from Pin-On-Disk Evaluations:

| Case | Disk Material | Pin (ball) Material | Sliding Distance (m) | Volume of Disk Removed (mm$^3$) | Volume of Pin Removed (×10$^3$ mm$^3$) |
|---|---|---|---|---|---|
| 1 | BG-42 | BG-42 | 237.6 | 3.82 | 3.90 |
| 2 | BG-42 | TiC 440C | 221.5 | 5.01 | 0.05 |
| 3 | C BG-42 | TiC 440C | 221.6 | 15.83 | 0.20 |
| 4 | C BG-42 | BG-42 | 227.0 | 2.43 | 0.49 |
| 5 | DLC BG-42 | BG-42 | 221.6 | 3.83 | 0.56 |
| 6 | DLC BG-42 | TiC 440C | 221.6 | 1.32 | 0.00 |

In Table 1, both "C" and "DLC" refer to ion treatment of the BG-42 raceway. "C" (cases 3 and 4) refers to a $4 \times 10^{17}$ ions/cm$^2$ dose of carbon delivered at 160 kev, whereas "DLC" (cases 5 and 6) refers to a $3 \times 10^{18}$ ions/cm$^2$ dose of carbon delivered at 90 kev.

The test conditions for the case samples shown in Table 1 were as follows. The diameter of the TiC ball was 1/8", while the diameter for the BG-42 ball was 3/32". The contact pressure in all cases was 1.4 GPa. Only a single sample (n=1) was used for each case.

Figure 5:
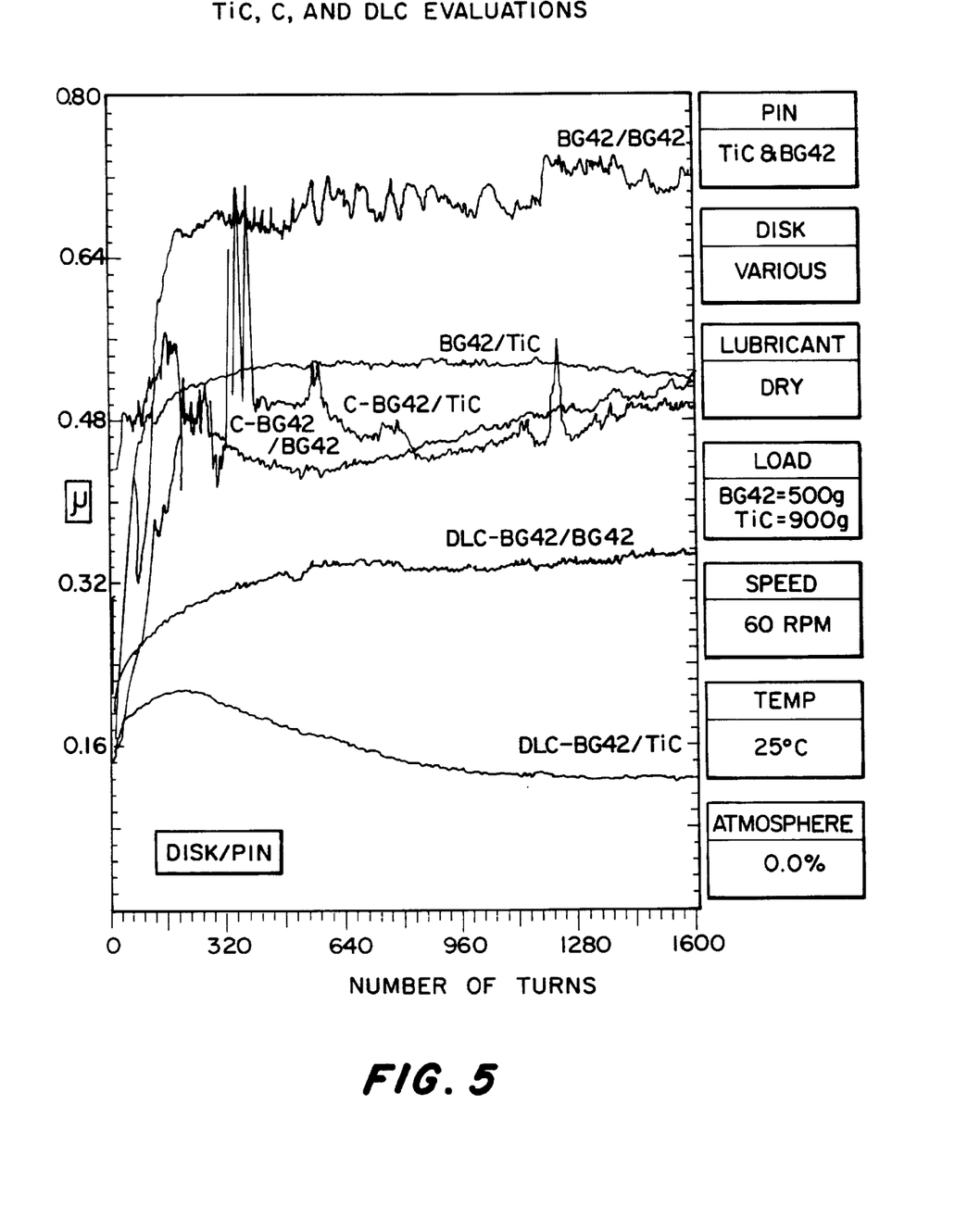
FIG. 5 is a graph showing the friction coefficient for different material combinations studied in the pin and disk tests.

FIG. 5 is a graph showing the friction coefficient ($\mu$) as a function of the number of turns for each of the cases listed in Table 1. Friction results from FIG. 5 show that there is a profound reduction in the friction coefficient when a DLC BG-42 stainless steel disk travels against a TiC-coated pin (DLC-BG42/TiC). In this case, there are comparatively small fluctuations in the timedependence of the friction coefficient, indicating negligible grabbing and slipping of the pin on the disk during the test. Furthermore, as shown in Table 1, the DLCs BG-42/TiC case generated no measurable wear volume from the pin, and relatively minimal wear volume from the disk.

The results for the DLC-BG42/TiC remain striking even in comparison to the other cases having either a DLC disk or a TiC-coated pin, but not both. The results indicate that a bearing couple combining a TiC-coated surface with a DLC surface, or more generally, a ceramic surface with an ion-implanted surface, produces profound reductions in wear and friction.

To improve the statistical significance of the results above, a second set of pin-on-disk tests were repeated for case 1 (BG42/BG42, referred to as the control case) and case 6 (DLC-BG42/TiC, referred to as the treated case) from Table 1. In these subsequent tests, there were five samples for each test combination (n=5). A summary of the results are shown in Table 2. In these subsequent tests, the 1/8" TiC ball had a 340 gram load and the 3/32" BG-42 ball had a 189 gram load, each resulting in a contact pressure of 1.0 Gpa. The results were obtained for 1600 cycles of the disk at 60 rpm.

In the columns of Table 2, SD refers to the standard deviation, which is shown in parenthesis. The mean values were calculated by paired two sample t-tests. The p-values were calculated using a two-tailed analysis, where normality of the data is not assumed. The p-value is a measure of the statistical significance of the results for the n=5 tests. The smaller the p-value, the more likely the means are significantly different between the two groups. For information on statistical analysis and p-values, see: Pagano et al., *Principles of Biostatistics* (Duxbury Press, Belmont Calif., 1992).

TABLE 2

Wear Data from Pin-On-Disk Evaluations:

| Wear Parameter | Treated (Case 6) Mean (SD) | Control (Case 1) Mean (SD) | Difference Mean (SD) | p-value |
|---|---|---|---|---|
| Friction Coefficient | 0.21 (0.01) | 0.74 (0.04) | −0.53 (0.04) | $1.0 \times 10^{-5}$ |
| Pin Wear Volume (mm3) | 0.02 (0.01) | 8.42 (1.86) | −8.39 (1.86) | $5.0 \times 10^{-4}$ |
| Disk Wear Area ($\mu m^2$) | 8.38 (2.15) | 15.2 (1.69) | −6.80 (3.10) | $8.0 \times 10^{-3}$ |

The results in Table 2 and the small p-values reaffirmed that there is a profound reduction in wear and friction for the combination of a TiC-coated surface and a DLC surface.

Implantable Heart Pump Using the Wear-Resistant Bearings

Implantable heart pumps are in continuous use for periods of up to five years or longer. It is critically important that bearings used in an implantable heart pump be wear-resistant. If not, wear over time will increase friction in the heart pump, reducing its ability to pump blood and thereby endangering the life of the user. Furthermore, even if bearing wear is recognized before endangering the user, the defective pump needs to be replaced, and this is a delicate and complicated surgical procedure that also endangers the user.

In general, heart pumps include a motor or actuator that transfers one type of power, e.g. electrical or compressed air, into some type of mechanical motion that ultimately drives a displacement element such as a diaphragm or bladder or axial rotary screw type pump to empty a blood chamber in the heart pump. The actuator includes at least one moving element for providing the mechanical motion. Bearings support the moving elements within the pump and minimize friction between the moving elements and stationary elements coupled to them.

For example, an implantable left ventricular-assist device may include a torque motor and a main rotor bearing. The main rotor bearing permits rotational motion of the torque motor relative to its stationary support structure. The main rotor bearing also reacts out loads on the motor that accrue from pressurizing a blood chamber and elements of wobble. This permits fine clearances between magnets of the torque motor and a stator having coil windings to drive the torque motor. The implantable heart pump may also include a mechanism that converts rotational motion from the torque motor into linear motion to drive a pusher plate which is connected to the diaphragm that pushes blood. Bearings may also be used in this mechanism to support the elements that carry out the rotational and linear motion. An example of an electric motor-driver, diaphram-pump type left ventricular-assist device is shown in "An Engineer for the Long Haul," *Design News*, p. 66–76 (Feb. 10, 1992).

The material combinations described above that exhibit reduced wear and friction are especially suitable for bearings used in heart pumps, particularly, an implantable ventricular-assist device of the type referred to above. In particular, ball bearings used in a ventricular-assist device may advantageously employ titanium carbide coated 440C stainless steel balls rolling on a BG-42 stainless steel raceway implanted with carbon ions to a density of about $3 \times 10^{18}$ ions/cm$^2$ at a beam energy of about 90 keV.

Other Embodiments

It is to be understood that while the invention has been described in conjunction with the detailed description thereof, that the foregoing description is intended to illustrate and not limit the scope of the invention, which is defined by the scope of the appended claims. For example, the ceramic coating can be applied to the raceway of a bearing and ion implantation performed on the rolling element of a bearing rather than vice versa. Also, rather than coating a stainless steel ball with a ceramic material the entire ball (or, more generally, bearing component) can be made out of a ceramic material.

In general, other embodiments can also include various rolling contact geometries, non-rolling contact bearings, the addition of lubricants, ceramic coatings other than titanium carbide, other implanted ion species, densities or energies. Bearings using the material combinations described above can be used for any application requiring long life.

Other aspects, advantages, and modifications are within the scope of the following claims.

What is claimed is:

1. A bearing comprising:
  a first component having a surface of ceramic material; and
  a second component having a surface implanted with ions and movable relative to said surface of said first component, said surfaces contacting each other when said components are at rest relative to each other and wherein the second component is a BG-42 stainless steel raceway.

2. The bearing of claim 1 wherein the surface of said second component is implanted with carbon ions.

3. The bearing of claim 2 wherein the surface of said second component is implanted with carbon ions to a density greater than about $1 \times 10^{18}$ ion/cm$^2$.

4. The bearing of claim 2 wherein the surface of said second component is implanted with carbon ions to a density of about $3 \times 10^{18}$ ion/cm$^2$.

5. The bearing of claim 2 wherein penetration of the carbon ions into the surface of said second component corresponds to carbon ion implantation at a beam energy of greater than about 50 keV.

6. The bearing of claim 1 wherein the ceramic material is selected from the group consisting of titanium carbide, titanium nitride and silicon nitride.

7. The bearing of claim 1 wherein the ceramic material comprises titanium carbide.

8. The bearing of claim 1 wherein the first component is a ball.

9. The bearing of claim 1 wherein the first component is a rolling element.

10. The bearing of claim 1 wherein the first component is a metal rolling element.

11. The bearing of claim 1 wherein the first component is a 440C stainless steel ball.

12. A bearing comprising:
  a titanium-carbide coated 440C stainless steel ball contacting, when at rest, a BG-42 stainless steel raceway implanted with carbon ions to a density greater than about $1 \times 10^{18}$ ions/cm$^2$ at a beam energy of greater than about 50 keV.

13. A bearing for use in an implantable heart pump, said bearing comprising:
  a first component having a surface of ceramic material; and
  a second component having a surface implanted with ions and movable relative to said surface of said first component, said surfaces contacting each other when said components are at rest relative to each other and wherein the second component is a BG-42 stainless steel raceway.

14. The bearing of claim 13 wherein the surface of said second component is implanted with carbon ions.

15. The bearing of claim 14 wherein the surface of said second component is implanted with carbon ions to a density greater than about $1\times10^{18}$ ion/cm$^2$.

16. The bearing of claim 14 wherein the surface of said second component is implanted with carbon ions to a density of about $3\times10^{18}$ ion/cm$^2$.

17. The bearing of claim 14 wherein penetration of the carbon ions into the surface of said second component corresponds to carbon ion implantation at a beam energy of greater than about 50 keV.

18. The bearing of claim 13 wherein the ceramic material is selected from the group consisting of titanium carbide, titanium nitride and silicon nitride.

19. The bearing of claim 13 wherein the ceramic material comprises titanium carbide.

20. The bearing of claim 13 wherein the first component is a ball.

21. The bearing of claim 13 wherein the first component is a rolling element.

22. The bearing of claim 13 wherein the first component is a metal rolling element.

23. The bearing of claim 13 wherein the first component is a 440C stainless steel ball.

24. A bearing for use in an implantable heart pump, said bearing comprising:

a titanium-carbide coated 440C stainless steel ball contacting, when at rest, a BG-42 stainless steel raceway implanted with carbon ions to a density greater than about $1\times10^{18}$ ions/cm$^2$ at a beam energy of greater than about 50 keV.

* * * * *